(12) United States Patent
Nishikaze

(10) Patent No.: US 12,110,309 B2
(45) Date of Patent: *Oct. 8, 2024

(54) METHOD FOR PREPARING ANALYTICAL SAMPLE, ANALYSIS METHOD, AND KIT FOR PREPARING ANALYTICAL SAMPLE

(71) Applicant: SHIMADZU CORPORATION, Kyoto (JP)

(72) Inventor: Takashi Nishikaze, Kyoto (JP)

(73) Assignee: SHIMADZU CORPORATION, Kyoto (JP)

( * ) Notice: Subject to any disclaimer, the term of this patent is extended or adjusted under 35 U.S.C. 154(b) by 86 days.

This patent is subject to a terminal disclaimer.

(21) Appl. No.: 16/590,676

(22) Filed: Oct. 2, 2019

(65) Prior Publication Data

US 2020/0109159 A1    Apr. 9, 2020

(30) Foreign Application Priority Data

Oct. 3, 2018  (JP) ................ 2018-188588

(51) Int. Cl.
*C07H 1/00* (2006.01)
*G01N 33/68* (2006.01)

(52) U.S. Cl.
CPC ........... *C07H 1/00* (2013.01); *G01N 33/6848* (2013.01); *G01N 2400/00* (2013.01); *G01N 2440/38* (2013.01); *G01N 2560/00* (2013.01)

(58) Field of Classification Search
None
See application file for complete search history.

(56) References Cited

U.S. PATENT DOCUMENTS

| 2018/0059094 A1 | 3/2018 | Nishikaze |
| 2018/0180627 A1 | 6/2018 | Nishikaze |

FOREIGN PATENT DOCUMENTS

| CN | 107430113 A | 12/2017 | |
| CN | 108132180 A | 6/2018 | |
| EP | 3 279 655 A1 | 2/2018 | |
| EP | 3343225 A1 | 7/2018 | |
| JP | 6135710 B2 | 5/2017 | |
| JP | 2018-109525 A | 7/2018 | |
| WO | WO 2015/075139 | * 5/2015 | ............ C08B 37/00 |
| WO | 2016159291 A1 | 10/2016 | |

OTHER PUBLICATIONS

Li, H. et al. MALDI-MS analysis of sialylated N-glycan linkage isomers using solidphase two step derivatization method, Analytica Chemica Acta, 924 (2016) 77-85 (Year: 2016).*

(Continued)

*Primary Examiner* — Xiaoyun R Xu
(74) *Attorney, Agent, or Firm* — Sughrue Mion, PLLC (57) ABSTRACT

A method for preparing an analytical sample for analysis of a glycan contained in a sample includes: performing an amidation reaction that amidates a lactone structure included in the glycan through contacting the sample with a reaction solution that is basic; adding an acidic solution to the reaction solution after the reaction solution is subjected to the amidation reaction; and purifying the sample contained in the reaction solution after the acidic solution is added to the reaction solution by using a carrier for hydrophilic interaction chromatography.

15 Claims, 5 Drawing Sheets

(56) References Cited

OTHER PUBLICATIONS

Takashi Nishikaze, et al., "Differentiation of Sialyl Linkage Isomers by One-Pot Sialic Acid Derivatization for Mass Spectrometry-Based Glycan Profiling", ACS Publications, American Chemical Society, 2017, pp. 2353-2360.

Takashi Nishikaze, "A universal approach to linkage-specific derivatization for sialic acids on glycopeptides", Journal of the American Society for Mass, 2017, 1 page.

Communication dated Mar. 4, 2020, from the European Patent Office in application No. 19201237.5.

Communication dated Jan. 5, 2022, issued by the Japanese Patent Office in application No. 2018-188588.

Communication dated May 9, 2022 from the State Intellectual Property Office of P.R. of China in Application No. 201910934909.7.

First Office Action dated Dec. 23, 2022 issued for the corresponding European Patent Application No. 19201237.5.

Chinese Office Action dated Jul. 31, 2023 in Chinese Application No. 201910934909.7.

\* cited by examiner

METHOD FOR PREPARING ANALYTICAL SAMPLE, ANALYSIS METHOD, AND KIT FOR PREPARING ANALYTICAL SAMPLE

INCORPORATION BY REFERENCE

The disclosure of the following priority application is herein incorporated by reference: Japanese Patent Application No. 2018-188588 filed Oct. 3, 2018

TECHNICAL FIELD

The present invention relates to a method for preparing an analytical sample, an analysis method, and a kit for preparing an analytical sample.

BACKGROUND ART

In analyzing a sample containing a glycan through mass spectrometry or the like, the glycan is purified with a carrier for hydrophilic interaction chromatography (hereinafter, referred to as "HILIC," as appropriate) to prepare an analytical sample (see PTL1 and NPTL1).

CITATION LIST

Patent Literature

PTL1: Japanese Patent No. 6135710 B

Non-Patent Literature

NPTL1: Nishikaze T, Tsumoto H, Sekiya S, Iwamoto S, Miura Y, Tanaka K. "Differentiation of Sialyl Linkage Isomers by One-Pot Sialic Acid Derivatization for Mass Spectrometry-Based Glycan Profiling" Analytical Chemistry, (U.S.), ACS Publications, Feb. 21, 2017, Volume 89, Issue 4, pp. 2353-2360

SUMMARY OF INVENTION

Technical Problem

The present inventor has found a method for suitably amidating sialic acid by using a basic solution in preparation of an analytical sample to analyze sialic acid included in a glycan. If a basic solution obtained after the reaction is diluted with an organic solvent containing about 0.1% by weight of trifluoroacetic acid, as described in PTL1, and purified with a HILIC carrier, however, problems arise such as a lower recovery rate for the glycan and significant appearance of peaks corresponding to contaminants in a mass spectrum.

Solution to Problem

According to the 1st aspect of the present invention, a method for preparing an analytical sample for analyzing a glycan contained in a sample comprises: performing an amidation reaction that amidates a lactone structure included in the glycan through contacting the sample with a reaction solution that is basic; adding an acidic solution to the reaction solution after the amidation reaction; and purifying the sample contained in the reaction solution by using a carrier for hydrophilic interaction chromatography after the acidic solution is added to the reaction solution.

According to the 2nd aspect of the present invention, in the method for preparing an analytical sample according to the 1st aspect, it is preferred that pH of the reaction solution after the acidic solution is added to the reaction solution is 10 or lower.

According to the 3rd aspect of the present invention, it is preferred that the method for preparing an analytical sample according to the 1st or 2nd aspect further comprises performing a lactonization reaction that lactonizes at least a part of sialic acids included in the glycans before the amidation reaction.

According to the 4th aspect of the present invention, in the method for preparing an analytical sample according to the 3rd aspect, it is preferred that the lactonization reaction is performed through contacting the sample with a lactonization reaction solution containing a dehydration condensation agent.

According to the 5th aspect of the present invention, in the method for preparing an analytical sample according to the 4th aspect, it is preferred that the reaction solution to be used for the amidation reaction contains ammonia or an amine, the lactonization reaction solution further contains a nucleophilic agent that is reacted with a sialic acid included in the glycan, the nucleophilic agent is different from ammonia or the amine contained in the reaction solution to be used for the amidation reaction, and in the lactonization reaction, a part of the sialic acids is lactonized based on a linkage type of the sialic acid, and at least a part of the nucleophilic agent is linked to another part of the sialic acids through addition of the lactonization reaction solution to the sample.

According to the 6th aspect of the present invention, in the method for preparing an analytical sample according to any one of the 3rd to 5th aspects, it is preferred that at least one selected from the group consisting of $\alpha 2,3$-sialic acid, $\alpha 2,8$-sialic acid, and $\alpha 2,9$-sialic acid among the sialic acids is lactonized in the lactonization reaction.

According to the 7th aspect of the present invention, in the method for preparing an analytical sample according to the 5th aspect, it is preferred that $\alpha 2,3$-sialic acid is lactonized and a part of the nucleophilic agent is linked to $\alpha 2,6$-sialic acid through addition of the lactonization reaction solution to the sample in the lactonization reaction.

According to the 8th aspect of the present invention, in the method for preparing an analytical sample according to any one of the 1st to 7th aspects, it is preferred that the acidic solution is a solution containing 0.2% by weight or more of trifluoroacetic acid.

According to the 9th aspect of the present invention, an analysis method comprises: preparing an analytical sample by using the method for preparing an analytical sample according to any one of the 1st to 8th aspects; and analyzing the prepared analytical sample.

According to the 10th aspect of the present invention, in the analysis method according to the 9th aspect, it is preferred that the prepared analytical sample is analyzed through at least one of mass spectrometry and chromatography.

According to the 11th aspect of the present invention, a kit for preparing an analytical sample comprises: an acidic solution, wherein the kit is used for the method for preparing an analytical sample according to any one of the 1st to 8th aspects.

Advantageous Effects of Invention

The present invention enables accurate analysis of a glycan sample in the case that the glycan sample is contained in a basic solution and is to be purified with a HILIC carrier.

DESCRIPTION OF EMBODIMENTS

Hereinafter, embodiments of the present invention will be described with reference to the drawings. In methods for preparing an analytical sample (sample for analysis) in embodiments below, a glycan contained in a sample is amidated with a basic reaction solution, an acidic solution is added to the solution containing the sample after the reaction, and the glycan is then purified with a HILIC carrier.

First Embodiment

In a method for preparing an analytical sample in the first embodiment, a sample containing a glycan is subjected to modification depending on a linkage type of sialic acid included in the glycan. This modification is performed as reaction in two stages, where sialic acid is amidated through the second-stage reaction and the glycan contained in the sample is then purified with a HILIC carrier.

Sialic acid is a saccharide abundant in a biological body. Sialic acid is included in glycans linked to protein in the biological body, and is often present at a non-reducing end of a glycan. Thus, sialic acid is positioned in the outermost side of such a glycoprotein molecule, and plays an important role because it is directly recognized by other molecules.

Sialic acid may have different linkage types to the adjacent saccharide. For example, α2,3- and α2,6-linkage types are primarily known for human N-linked glycans (N-glycans), and in addition to these linkage types, α2,8- and α2,9-linkage types are known for O-linked glycans (O-glycans) and glycosphingolipids. Sialic acids with such different linkage types are recognized by different molecules, and thus can play different roles.

Analysis of a sialylated glycan containing sialic acid by mass spectrometry is not easy because sialic acid is less likely to be ionized in the positive ion mode due to its negative charge and is easily decomposed. In addition, type-by-type analysis of the linkage type of sialic acid is more difficult because molecular weights are identical among sialic acids with different linkage types. For this reason, chemical modification methods to modify in a linkage type-specific manner are performed to stabilize sialic acids for type-by-type analysis of the linkage type of sialic acid.

Figure 1:
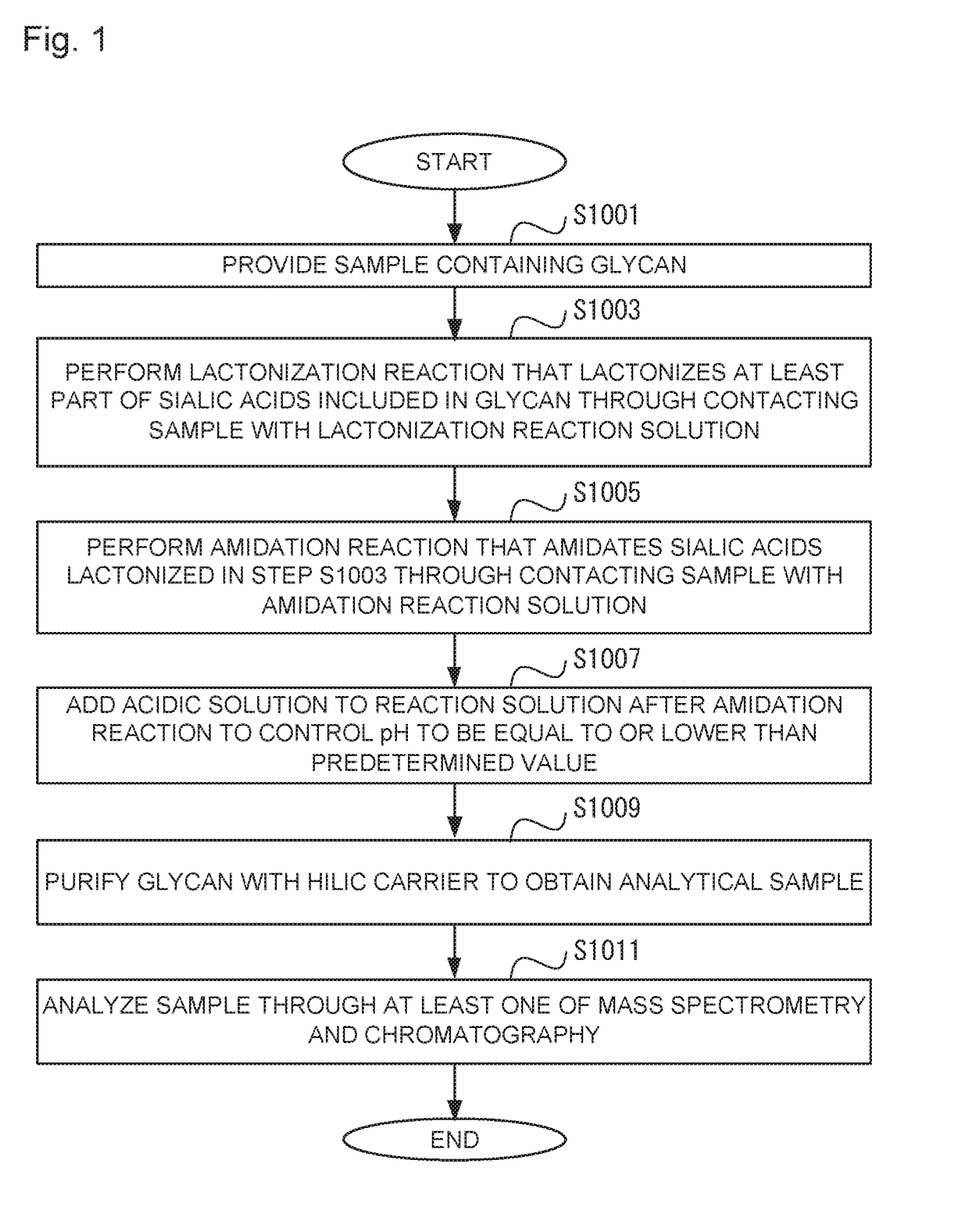
FIG. 1 shows a flowchart illustrating a procedure of an analysis method according to one embodiment.

FIG. 1 shows a flowchart illustrating the procedure of an analysis method according to the method for preparing an analytical sample in the present embodiment. In this analysis method, a chemical modification method is used for type-by-type analysis of the linkage type of sialic acid. A sample containing a glycan is prepared in a step S1001.

The sample containing a glycan is not particularly limited, and may contain at least one molecule selected from the group consisting of a free glycan, a glycopeptide and a glycoprotein, and a glycolipid. The method for preparing an analytical sample according to the present embodiment is suitably used for analysis of sialic acid included in a glycan. Hence, it is preferable for the glycans in the sample to contain a glycan which may have sialic acid at an end such as an N-linked glycan, an O-linked glycan, and a glycolipid-type glycan. It is more preferable for the glycans in the sample to include at least one of α2,3-sialic acid, α2,8-sialic acid, and α2,9-sialic acid, which are likely to be lactonized.

If a sample containing a free glycan is used, the glycan may be a glycan released from a glycoprotein or a glycopeptide, or a glycolipid. Examples of a method that can be used to release a glycan from a glycoprotein, a glycopeptide, or a glycolipid include enzymatic treatment using N-glycosidase, O-glycosidase, or endoglycoceramidase, and a method such as hydrazinolysis or β-elimination by alkali treatment. In releasing an N-linked glycan from the peptide chain of a glycopeptide or a glycoprotein, enzyme treatment is suitably used, for example, with peptide-N-glycosidase F (PNGase F), peptide-N-glycosidase A (PNGase A), or endo-β-N-acetylglucosaminidase (Endo M). Alternatively, modification such as pyridylamination (PA labeling) can be appropriately performed for a reducing end of the glycan. Cleavage of the peptide chain of a glycopeptide or a glycoprotein, which is described later, may be performed before the enzyme treatment.

If the sample contains a glycopeptide or a glycoprotein, treatment to suppress a side reaction of the peptide moiety can be appropriately performed, as described later in the section "Suppression of Side Reaction of Glycopeptide and Glycoprotein". In the case that the peptide chain of a glycopeptide or a glycoprotein includes a large number of amino acid residues, it is preferable to cleave the peptide chain in use, for example, through enzymatic cleavage. In preparing a sample for mass spectrometry, for example, the number of amino acid resides in the peptide chain is preferably 30 or less, more preferably 20 or less, and even more preferably 15 or less. In the case that the origin of peptide to which a glycan is linked is needed to be clarified, the number of amino acid resides in the peptide chain is preferably two or more, and more preferably three or more.

A digestive enzyme is used in cleaving the peptide chain of a glycopeptide or a glycoprotein, and examples thereof include trypsin, Lys-C, arginine endopeptidase, chymotrypsin, pepsin, thermolysin, proteinase K, and pronase E. Two or more of these digestive enzymes may be used in combination. Conditions for cleavage of the peptide chain are not limited, and a protocol suitable for the digestive enzyme to be used is appropriately employed. Before the cleavage, denaturation treatment or alkylation treatment may be performed for the protein or peptide in the sample. Conditions for the denaturation treatment or alkylation treatment are not particularly limited.

The cleavage treatment for the above peptide chain may be performed after a lactonization reaction in a step S1003 described later. The cleavage of the peptide chain may be achieved not through enzymatic cleavage but through chemical cleavage or any other method.

The completion of the step S1001 is followed by a step S1003.

Lactonization Reaction

In the step S1003, a lactonization reaction is performed (hereinafter, the expression "lactonization reaction" refers to the lactonization reaction in the step S1003, unless otherwise stated) that lactonizes at least a part of sialic acids included in the glycans through contacting the sample with a reaction solution for lactonization (hereinafter, referred to as "lactonization reaction solution"). In the lactonization reaction, a part of sialic acids which are less likely to be lactonized such as α2,6-sialic acid is preferably subjected to modification different from lactonization, and an example in which such modification is performed will be described below. In the lactonization reaction, α2,3-sialic acid, α2,8-sialic acid, and α2,9-sialic acid are suitably lactonized.

The lactonization reaction solution contains a dehydration condensation agent and a nucleophilic agent containing an alcohol, an amine, or a salt thereof. The types and concentrations of the dehydration condensation agent and nucleophilic agent are adjusted to selectively cause a dehydration reaction or a nucleophilic reaction based on the linkage type of sialic acid.

In the case that modification is not performed for sialic acids which are less likely to be lactonized such as α2,6-sialic acid, inclusion of the nucleophilic agent is not needed.

A lactone generated through intramolecular dehydration of the carboxy group of α2,3-sialic acid is a 6-membered ring, and a lactone that can be generated through intramolecular dehydration of the carboxy group of α2,6-sialic acid is a 7-membered ring. Six-membered rings are more stable than 7-membered rings, and thus α2,3-sialic acid, which generates a 6-membered ring, has a higher tendency to be lactonized than α2,6-sialic acid. The carboxy group of α2,3-sialic acid is present at a position causing relatively high steric hindrance as compared with the carboxy group of α2,6-sialic acid, and hence α2,3-sialic acid is less reactive with large molecules than α2,6-sialic acid. Based on such difference in molecular structure among the linkage types of sialic acids, the types and concentrations of the dehydration condensation agent and nucleophilic agent are adjusted to provide different modifications for different linkage types of sialic acids.

Dehydration Condensation Agent in Lactonization Reaction

It is preferable for the dehydration condensation agent to contain a carbodiimide. This is because when a carbodiimide is used, the carboxy group present at a site causing high steric hindrance is less likely to be amidated than in use of a phosphonium-based dehydration condensation agent (what is called BOP reagent) or an uronium-based dehydration condensation agent as the dehydration condensation agent. Examples of the carbodiimide include N,N'-dicyclohexylcarbodiimide (DCC), N-(3-dimethylaminopropyl)-N'-ethyl-carbodiimide (EDC), N,N'-diisopropylcarbodiimide (DIC), 1-tert-butyl-3-ethylcarbodiimide (BEC), N,N'-di-tert-butylcarbodiimide, 1,3-di-p-toluylcarbodiimide, bis(2,6-diisopropylphenyl)carbodiimide, bis(trimethylsilyl)carbodiimide, and 1,3-bis(2,2-dimethyl-1,3-dioxolan-4-ylmethyl)carbodiimide (BDDC), and salts thereof.

Additive in Lactonization Reaction

To promote dehydration condensation by the dehydration condensation agent and suppress a side reaction, a highly nucleophilic additive is preferably used in addition to the carbodiimide. The highly nucleophilic additive for use is preferably, for example, 1-hydroxybenzotriazole (HOBt), 1-hydroxy-7-aza-benzotriazole (HOAt), 4-(dimethylamino)pyridine (DMAP), ethyl 2-cyano-2-(hydroxyimino)acetate (CHA), N-hydroxy-succinimide (HOSu), 6-chloro-1-hydroxy-benzotriazole (Cl-HoBt), or N-hydroxy-3,4-dihydro-4-oxo-1,2,3-benzotriazine (HOOBt).

Nucleophilic Agent in Lactonization Reaction

The amine for use as the nucleophilic agent preferably contains a primary or secondary alkylamine having two or more carbon atoms. The primary alkylamine is preferably, for example, ethylamine, propylamine, isopropylamine, butylamine, sec-butylamine, or tert-butylamine. The secondary alkylamine is preferably, for example, dimethylamine, ethylmethylamine, diethylamine, propylmethylamine, or isopropylmethylamine. To lower the probability of the occurrence of amidation of a carboxy group present at a site with high steric hindrance such as the carboxy group of α2,3-sialic acid, use of an amine having a branched alkyl group (hereinafter, "branched" refers to a branch of a hydrocarbon chain) such as isopropylamine is preferred. If an amine is used as the nucleophilic agent in the lactonization reaction solution, the carboxy group of a part of sialic acids such as α2,6-sialic acid is amidated based on the linkage type of the sialic acid.

The alcohol for use as the nucleophilic agent is not particularly limited, and methanol, ethanol, or the like can be used. If an alcohol is used as the nucleophilic agent in the lactonization reaction solution, the carboxy group of a part of sialic acids such as α2,6-sialic acid is esterified based on the linkage type of the sialic acid.

The nucleophilic agent may contain a salt of any of the above nucleophilic agents.

Concentrations of Dehydration Condensation Agent and Nucleophilic Agent

For example, the concentration of the dehydration condensation agent in the lactonization reaction solution is preferably 1 mM to 5 M, and more preferably 10 mM to 3 M. If a carbodiimide and a highly nucleophilic additive such as HOAt or HOBt are used in combination, the concentration of each is preferably in the above range. The concentration of the nucleophilic agent in the lactonization reaction solution is preferably 0.01 to 20 M, and more preferably 0.1 M to 10 M. The reaction temperature during the lactonization reaction is preferably around −20° C. to 100° C., and more preferably −10° C. to 50° C. The time during which the sample is in contact with the lactonization reaction solution is adjusted on the basis of the concentrations of the sample and reagents, the reaction temperature, and so on, and, for example, about 30 minutes to several hours.

Phase for Lactonization Reaction

The lactonization reaction can be performed in either a liquid phase or a solid phase. The state of the sample in causing the lactonization reaction is not particularly limited as long as the state allows the sample to be in contact with the lactonization reaction solution.

If the reaction is performed in a solid phase, the solid phase carrier for use is not limited as long as the solid phase carrier is capable of immobilizing a glycan, a glycopeptide, a glycoprotein, or the like. To immobilize a glycopeptide or a glycoprotein, for example, a solid phase carrier having, as a ligand, an epoxy group, a tosyl group, a carboxy group, an amino group, or the like can be used. To immobilize a glycan, for example, a solid phase carrier having, as a ligand, a hydrazide group, an aminooxy group or the like can be used. It is also preferable to allow the glycan to be adsorbed on a carrier, in other words, a stationary phase for hydrophilic interaction chromatography (HILIC), and it is more preferable that the HILIC carrier include an amide group.

If the lactonization reaction is performed in a solid phase, after the sample immobilized to the solid phase carrier is subjected to an action of the lactonization reaction solution for lactonization, the sample can be suitably released and collected from a carrier, for example, through a chemical technique or an enzyme reaction. For example, a glycoprotein or a glycopeptide immobilized to the carrier may be enzymatically cleaved by using glycosidase such as PNGase F or a digestive enzyme such as trypsin and collected, and a glycan bonding to a solid phase carrier having a hydrazide group may be released and collected by using a weakly acidic solution. In HILIC, the sample can be subjected to a lactonization reaction with a lactonization reaction solution containing acetonitrile or the like as a solvent followed by elution with an aqueous solution such as water.

Reacting in a state in which the sample is immobilized to a solid phase carrier facilitates removal of the reaction solution and desalting and purification, and sample preparation can be simplified. In use of a solid phase carrier, the sample can be immobilized as the form of glycoprotein or glycopeptide and subjected to a lactonization reaction, and then cleaved with glycosidase such as PNGase F, as described above. Thereby, the sample after the lactonization reaction can be collected as free glycan.

As necessary, the sample after the lactonization reaction may be subjected to treatments such as purification, desalting, solubilization, concentration, and drying, for example, by using a known method. If the lactonization reaction was performed in a liquid phase, it is preferable to introduce the reaction solution into a HILIC column for purification of the glycan.

The completion of the step S1003 is followed by a step S1005.

Amidation Reaction

In the step S1005, an amidation reaction is performed (hereinafter, the expression "amidation reaction" refers to the amidation reaction in the step S1005, unless otherwise stated) that amidates a sialic acid lactonized by the lactonization reaction through contacting the sample with a reaction solution (hereinafter, referred to as "amidation reaction solution"). The present inventor has found a method for directly and quickly amidating a lactone, which is quite contrast to the common general knowledge of ring-opening of a lactone through hydrolysis followed by amidation of the carboxy group. This reaction is different from hydrolysis since the reaction suitably proceeds even under anhydrous conditions, and inferred to be aminolysis based on the interaction between an amino group and a lactone. Hereinafter, ring-opening and amidation of a lactone with ammonia, an amine, or a salt thereof, available even under anhydrous conditions, is referred to as "aminolysis".

The amidation reaction solution contains ammonia, an amine, or a salt thereof as a nucleophilic agent (hereinafter, referred to as "second nucleophilic agent," as appropriate). The second nucleophilic agent is different from the nucleophilic agent contained in the lactonization reaction solution (hereinafter, referred to as "first nucleophilic agent," as appropriate). In the case that an analytical sample obtained by using the method for preparing an analytical sample in the present embodiment is analyzed through mass spectrometry, the first nucleophilic agent and the second nucleophilic agent are selected so that they can be distinguished from each other through mass spectrometry, for example, so that they are different in mass. The first nucleophilic agent and the second nucleophilic agent are selected so that accurate mass separation is achieved for obtained modified products under the condition of mass resolution of mass spectrometry. The first nucleophilic agent and the second nucleophilic agent may be different substances, or identical substances to which different masses have been imparted by using stable isotopes. Alternatively, the first nucleophilic agent and the second nucleophilic agent may include an isobaric tag as represented by iTRAQ. In this case, such a tag is designed so that product ions obtained through cleavage performed between the first stage mass spectrometry and the second stage mass spectrometry have different values of m/z, and hence identification of the linkage type or a lactone form of sialic acid can be performed by using tandem mass spectrometry (MS/MS). Thus, in subjecting respective modified products modified with the first nucleophilic agent and the second nucleophilic agent to mass spectrometry in two or more stages, the modified products need to be separated in any of the stages by different values of m/z. In the case that an analytical sample obtained by using the method for preparing an analytical sample in the present embodiment is analyzed through chromatography, it is preferable for easy separation through chromatography that they have different substituents.

Amine in Amidation Reaction

If an amine is used as the second nucleophilic agent, the amine is preferably a primary amine, more preferably a primary amine having a linear hydrocarbon group, and even more preferably a primary amine having a linear alkyl group. The primary amine having a linear alkyl group as the amine contained in the amidation reaction solution is preferably a primary amine having 10 or less carbon atoms, more preferably a primary amine having seven or less carbon atoms, even more preferably methylamine, ethylamine, propylamine, butylamine, or pentylamine, and the most preferably methylamine. It is preferable for the amine contained in the amidation reaction solution to have a linear structure without any branch, or have a smaller number of carbon atoms, because the lactonized sialic acid is more efficiently amidated.

If the amine contained in the amidation reaction solution is a primary amine having an unsaturated linear hydrocarbon group, the unsaturated linear hydrocarbon group preferably includes a double bond, and more preferably includes an allyl group, and the amine is the most preferably allylamine. The amine contained in the amidation reaction solution may be a primary amine including a hydroxy group, and in this case the amine is preferably ethanolamine. The amine contained in the amidation reaction solution may include various functional groups other than an alkyl group. When a glycan is modified and provided with such a functional group as a result of the amidation reaction, the modified glycan can be separated more easily not only through mass spectrometry but also through chromatography or the like.

The amidation reaction solution may contain a salt of ammonia or the amine described above.

Dehydration Condensation Agent

The amidation reaction does not require any dehydration condensation agent, and may be free of a dehydration condensation agent. The amidation reaction is preferably performed only through contacting the sample with the amidation reaction solution, and thus the lactonized sialic acid can be stabilized through a simple operation in the amidation reaction.

Although the amidation reaction does not require any dehydration condensation agent, the amidation reaction solution may contain a dehydration condensation agent. For example, the amidation reaction solution containing a sample may be prepared by adding ammonia, an amine, or a salt thereof without removing the lactonization reaction solution added to the sample in the step S1003. In this case, operations are simplified by omitting the removal of the lactonization reaction solution.

Concentration of Amidation Reaction Solution

The concentration of ammonia, an amine, or a salt thereof in the amidation reaction solution is preferably 0.1 M (M denotes mol/L) or more, more preferably 0.3 M or more, even more preferably 0.5 M or more, further preferably 1.0 M or more, and the most preferably 3.0 M or more. In a preferred example, the amidation reaction solution contains ammonia or a primary amine, in particular, methylamine, and the concentration of ammonia or the primary amine such as methylamine is preferably 0.1 M or more, more preferably 0.3 M or more, even more preferably 0.5 M or more, further preferably 1.0 M or more, and the most preferably 3.0 M or more. The higher the concentration of amine or the like in the amidation reaction solution is, the more reliably the lactonized sialic acid can be amidated. The concentration of amine in the amidation reaction solution can be, for example, appropriately set to 50% or less.

Solvent of Amidation Reaction Solution

The solvent of the amidation reaction solution may be an aqueous solvent or an organic solvent. However, it is preferable for the solvent to have a lower water content in order to prevent hydrolysis of the lactone and cause amidation quickly and reliably. The solvent of the amidation reaction solution is preferably a dehydrated solvent, which has been subjected to a dehydration operation to reduce the water content, and more preferably an anhydrous solvent. The solvent of the amidation reaction solution preferably contains at least one of methanol and acetonitrile (ACN).

The amidation reaction solution may contain a significant amount of water ($H_2O$), and the solvent of the amidation reaction solution may be water.

pH of Amidation Reaction Solution

The pH of the amidation reaction solution is 7.7 or higher, more preferably higher than 8, even more preferably higher than 10, and further preferably 12 or higher. Higher pH is preferred for the amidation reaction solution because the lactone is more quickly and reliably amidated.

Time Needed for Amidation Reaction

The amidation reaction is completed within several seconds to several minutes. Thus, the time during which the sample is in contact with the amidation reaction solution in order to perform the amidation reaction of the lactone (hereinafter, referred to as "reaction time") is preferably shorter than 1 hour, more preferably shorter than 30 minutes, even more preferably shorter than 15 minutes, further preferably shorter than 5 minutes, and the most preferably shorter than 1 minute. It is suitable to wash the sample with the amidation reaction solution, or only to temporarily pass the amidation reaction solution through the sample held on a carrier or the like. Since the amidation reaction is completed within a short time in this way, deterioration of the quantitatively due to the decomposition of the lactone, which is unstable, can be prevented in analysis of the glycan. Through setting the reaction time of the amidation reaction short, analysis of the sample becomes more efficient.

Phase for Amidation Reaction

In the method for preparing an analytical sample in the present embodiment, the amidation reaction is performed in a liquid phase.

The completion of the step S1005 is followed by a step S1007.

Control of pH of Reaction Solution after Amidation Reaction

In the step S1007, an acidic solution to lower pH is added to the reaction solution after the amidation reaction (hereinafter, the expression "acidic solution" refers to the acidic solution to be added to the reaction solution in the step S1007) to control the pH of the reaction solution to be a predetermined value or lower. The predetermined value is preferably 10 or lower, and more preferably 8 or lower. For the predetermined value, pH suitable for a HILIC column to be used in a step S1009 is also preferable, and in particular it is more preferable to select from a range of pH recommended by the manufacturer or the like of the column (hereinafter, referred to as "recommended pH"). In the present embodiment, pH of lower than 7 is assumed as being acidic, and pH of higher than 7 as being basic. The pH of the acidic solution is more preferably 6 or lower, and even more preferably 4 or lower.

The composition of the acidic solution is not particularly limited and may be any composition that allows purification with a HILIC column, described later, and analysis through mass spectrometry or the like for the glycan with a desired accuracy. The type of acid contained in the acidic solution is not particularly limited, and, for example, trifluoroacetic acid (TFA) can be used because it is a strong acid soluble in organic solvents. The acidic solution is preferably a solution containing 0.2% by weight or more of TFA in an organic solvent, more preferably containing 1% by weight or more of TFA in an organic solvent, even more preferably containing 2.4% by weight or more of TFA in an organic solvent, further preferably containing 4% by weight or more of TFA in an organic solvent, and furthermore preferably containing 5% by weight or more of TFA in an organic solvent. The lower the pH of the acidic solution is, the more efficiently the pH of the reaction solution after the amidation reaction can be lowered. The above organic solvent constituting the acidic solution is preferably acetonitrile, but not particularly limited thereto. The acidic solution may contain water, as appropriate.

As demonstrated in Comparative Examples described later, if only dilution or the like with an organic solvent is performed as with the case of a conventional operation performed before purification with a HILIC column, purification with a HILIC column after the amidation reaction causes reduction of the sample recovery rate and the appearance of peaks corresponding to contaminants in the mass spectrum. Through adjustment of the pH of the reaction solution after the amidation reaction with the method for preparing an analytical sample in the present embodiment, however, the sample recovery rate was improved and peaks corresponding to contaminants in the mass spectrum were weakened as demonstrated in Examples.

The completion of the step S1007 is followed by a step S1009.

Purification of Glycans Using HILIC Carrier

In the step S1009, the reaction solution the pH of which has been controlled in the step S1007 is introduced into a HILIC column, and the glycan is purified with a HILIC carrier in the column. After this operation, an analytical sample is obtained. After the reaction solution the pH of which has been controlled is introduced into the HILIC column and the glycan is adsorbed on the carrier, washing is performed appropriately through passing a liquid, and then water, aqueous solution, or the like is introduced into the column to raise the concentration of water or polar solvent, eluting the sample containing the glycan.

The HILIC column in the present embodiment is not particularly limited as long as the column is capable of purifying the glycan in the sample after the amidation reaction, but is preferably a pretreatment column, for example, for solid phase extraction. Various types of pretreatment columns can be used, such as pipette tip-type columns, spin columns, syringe-type columns, and well plate-type columns.

A trap column, which is used for concentration or the like of an analytical sample before the sample is introduced into an analysis column in LC/MS, may be used for the HILIC column. Purification may be performed in a batch-mode method in which a HILIC carrier is introduced into a container containing a sample for adsorption.

The carrier in the HILIC column is not particularly limited as long as the carrier is capable of purifying the glycan in the sample after the amidation reaction. The carrier preferably contains unmodified silica or silica gel or the like modified with a polar functional group such as an aminopropyl group, an amide group, diol, a cyano group, a polysuccinimide derivative, and cyclodextrin. It is preferable for the carrier to have an amide group in order to suitably separate the sample containing an amidated glycan. Alternatively, the carrier in the HILIC column may be a polysaccharide-based carrier containing cellulose, sepharose, agarose, or the like. As another example, the carrier in the HILIC column may contain silica gel or polymer having a plurality of ionic functional groups such as a sulfo group and a quaternary ammonium.

As necessary, the sample after the purification with the HILIC carrier may be subjected to purification, solubilization, desalting, concentration, drying, and so on, by using a known method or the like.

Through the above-described preparation method, sialic acids which are of a linkage type less likely to be lactonized, such as $\alpha 2,6$-sialic acid, are modified with the first nucleophilic agent in the lactonization reaction. Sialic acids which are of a linkage type likely to be lactonized, such as $\alpha 2,3$-, $\alpha 2,8$-, and $\alpha 2,9$-sialic acids, are lactonized in the lactonization reaction, and modified with the second nucleophilic agent in the amidation reaction.

The completion of the step S1009 is followed by a step S1011.

In the step S1011, the sample is analyzed through at least one of mass spectrometry and chromatography. Glycans respectively subjected to modification with the first nucleophilic agent and the second nucleophilic agent through the above-described lactonization reaction and amidation reaction have different masses. Accordingly, these glycans can be separated through mass spectrometry on the basis of the linkage type of sialic acid.

The ionization method in the mass spectrometry is not particularly limited, and matrix-assisted laser desorption/ionization (MALDI), electrospray ionization (ESI), nano-electrospray ionization (nano-ESI), or the like can be used. MALDI is particularly preferred for the ionization method. In ionization in the mass spectrometry, either the positive ion mode or the negative ion mode may be used. The mass spectrometry may be performed in multiple stages, which suitably allows analysis of the structure of a glycan in addition to the linkage type of sialic acid, or the structure of the peptide chain.

If analysis is performed through chromatography, liquid chromatography is preferable. The column for liquid chromatography is not particularly limited, and a hydrophobic reverse phase column such as C30, C18, C8, or C4, a carbon column, a normal phase column for HILIC, or any other column can be appropriately used. It is preferred that after liquid chromatography is performed, measurement is performed by mass spectrometry to precisely analyze components in the sample through multiple separation. In this case, it is more preferred that an eluate from a liquid chromatograph is directly ionized by, for example, ESI in a mass spectrometer under online control.

The data acquired through mass spectrometry or chromatography are analyzed. This analysis includes quantification of glycans including sialic acids which are likely to be lactonized, such as $\alpha 2,3$-sialic acid, and glycans including sialic acids which are less likely to be lactonized, such as $\alpha 2,6$-sialic acid, in a type-by-type fashion with respect to the linkage type, generation of data corresponding to the mass spectrum, and so on. The method for analyzing the data acquired through mass spectrometry or chromatography is not particularly limited.

At the completion of the step S1011, the procedure is terminated.

Suppression of Side Reaction of Glycopeptide and Glycoprotein

In the case that the lactonization reaction solution and amidation reaction solution are added to a glycopeptide or a glycoprotein to modify sialic acid as described above, a side reaction may occur, such as intramolecular dehydration condensation between an amino group and a carboxy group present in the side chain of an amino acid or at an end of the peptide backbone in the glycopeptide or glycoprotein. In this case, the mass spectrum peak corresponding to a glycan to be analyzed is split, which disadvantageously complicates analysis.

The present inventor has revealed that the side reaction of a peptide moiety is primarily derived from the presence of an amino group, and that preliminary blocking of amino groups, for example, by using chemical modification, before modification of sialic acid can suppress the side reaction of a peptide moiety in modification of sialic acid. For the details, see the following literature: Takashi Nishikaze, Sadanori Sekiya, Shinichi Iwamoto, Koichi Tanaka. "A Universal Approach to linkage-Specific Derivatization for Sialic Acids on Glycopeptides," Journal of The American Society for Mass Spectrometry, June, 2017, Volume 28, Issue 1 Supplement, Poster No. MP091. The method for preparing an analytical sample in the present embodiment can be applied to a glycopeptide and a glycoprotein in a similar way. Specifically, a glycopeptide or a glycoprotein is subjected to a reaction to block amino groups such as dimethylamidation or guanidinylation, and then to the lactonization reaction and amidation reaction. If a method for forming a lactone according to the linkage type of sialic acid is then used, the linkage type of sialic acid can be identified.

Some glycopeptides are inherently less likely to undergo a side reaction due to the properties based on the amino acid sequence. For example, a glycopeptide generated through digestion of the Fc region of IgG with a digestive enzyme such as trypsin does not include lysine, and the amino groups at the N-terminals quickly undergo cyclodehydration to be pyroglutamylated in the presence of a dehydration condensation agent. As a result, the amino groups are eliminated, and thus preliminary blocking of amino groups by dimethylamidation, guanidinylation or the like is unnecessary. For such a glycopeptide, a mass spectrum sufficient for analysis can be acquired through a lactonization reaction and an amidation reaction without blocking of amino groups.

Kit for Preparing Analytical Sample

Provided is a kit for preparing an analytical sample (hereinafter, referred to as "preparation kit") which is suitably used for the method for preparing an analytical sample in the present embodiment. The contents of the preparation kit are not particularly limited as long as the above-described acidic solution to control the pH of the reaction solution after the amidation reaction is contained, and the kit can contain a reagent or any consumable other than reagents for mass spectrometry. By using the preparation kit, an analytical sample can be more efficiently prepared.

According to the above-described embodiment, it is possible to obtain the following functions and effects.

(1) The method for preparing an analytical sample in the present embodiment includes: performing an amidation reaction that amidates a lactone structure included in a glycan through contacting a sample with a reaction solution that is basic; adding an acidic solution to the reaction solution after the amidation reaction; and purifying the sample contained in the reaction solution by using a HILIC carrier after the acidic solution is added to the reaction solution. This can improve the sample recovery rate for the sample subjected to the amidation reaction and HILIC and reduce contaminants, allowing analysis with high accuracy.

(2) The method for preparing an analytical sample in the present embodiment includes performing an lactonization reaction that lactonizes at least a part of sialic acids included in the glycans before the amidation reaction. Thereby, the sialic acids lactonized in the lactonization reaction can be quickly modified through the amidation reaction.

(3) In the method for preparing an analytical sample in the present embodiment, the lactonization reaction is performed through contacting the sample with a lactonization reaction solution containing a dehydration condensation agent. Thereby, sialic acids which are likely to be lactonized and sialic acids which are less likely to be lactonized can be modified while distinguished from each other.

(4) In the method for preparing an analytical sample in the present embodiment, the reaction solution to be used for the amidation reaction contains ammonia or an amine, the lactonization reaction solution further contains a first nucleophilic agent that is reacted with a sialic acid included in the glycan, the first nucleophilic agent is different from ammonia or the amine contained in the reaction solution to be used for the amidation reaction, and in the lactonization reaction, a part of the sialic acids is lactonized based on the linkage type of the sialic acid and at least a part of the first nucleophilic agent is linked to another part of the sialic acids through addition of the lactonization reaction solution to the sample. This enables type-by-type analysis of the linkage type of sialic acid based on the difference in mass or the like.

(5) In the method for preparing an analytical sample in the present embodiment, the acidic solution is a solution containing 0.2% by weight or more of trifluoroacetic acid (TFA). Utilizing the property of TFA as a strong acid soluble in organic solvents, this enables reliable and efficient adjustment of the pH of the reaction solution after the amidation reaction.

(6) The analysis method according to the present embodiment includes: preparing an analytical sample by using the method for preparing an analytical sample in the present embodiment; and analyzing the prepared analytical sample. This can improve the sample recovery rate in purification using a HILIC column and reduce contaminants, allowing analysis of a glycan with high accuracy.

(7) In the analysis method according to the present embodiment, the prepared analytical sample can be analyzed through at least one of mass spectrometry and chromatography. This enables type-by-type analysis of the linkage type of sialic acid for a glycan based on the difference in mass caused in a linkage type-specific manner and its impact on separation through chromatography.

(8) The kit for preparing an analytical sample according to the present embodiment includes an acidic solution. Thereby, the sample to be introduced into a HILIC column can be quickly provided or prepared after the amidation reaction.

A variation as shown below also falls within the scope of the present invention, and can be combined with the above-described embodiment. In the following Variation, a site or the like having the same structure or function as in the above-described embodiment is referred to with the same reference sign, and description is omitted as appropriate.

Variation 1

In the above-described embodiment, the sialic acid lactonized through the lactonization reaction is amidated through the amidation reaction. In the situation that the sample is to be purified by using a HILIC carrier after performing the amidation reaction, however, there is no limitation to treatment before the amidation reaction. For example, the amidation reaction may be performed without performing the lactonization reaction to detect lactonized sialic acid originally contained in the sample. Alternatively, the lactonization reaction may be performed in a manner nonspecific to the linkage type of sialic acid.

The present invention is not limited to the contents of the above-described embodiment. Other embodiments within the scope of the technical idea of the present invention are also included in the scope of the present invention.

EXAMPLES

Hereinbelow, examples of the present embodiment will be described. However, the present invention is not limited to the following Examples. Hereinafter, "%" denotes "% by weight" unless otherwise stated.

Figure 2A:
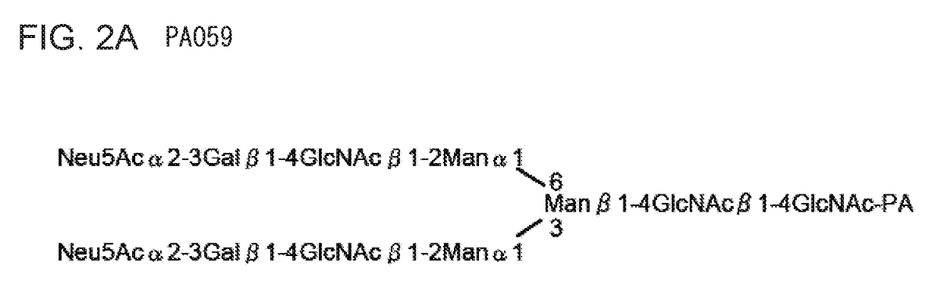
FIG. 2A shows a diagram illustrating a structure of a glycan used in a Comparative Example.

Comparative Example 1: Comparative Example Using Acidic Glycan Lactonization Reaction and Amidation Reaction The PA-labeled glycan PA059 (the structure is illustrated in FIG. 2A) purchased from Masuda Chemical Industries Co., LTD. was prepared as a sample. PA059 is a biantennary glycan including two α2,3-sialic acids, and hereinafter referred to as "PAm059." The sample 200 fmol is subjected to evaporation to dryness in a Eppendorf tube, and 20 μL of a lactonization reaction solution containing isopropylamine (2M isopropylamine hydrochloride, 500 mM EDC-HCl, 500 mM HOBt) was then added thereto, and reacted with stirring at 2000 rpm for 1 hour (through this operation, α2,6-sialic acid and α2,3-sialic acid were to be converted to isopropylamide and lactone form, respectively, and the two sialic acids of PAm059 were to be lactonized because they were each α2,3-sialic acid). After the lactonization reaction, 20 μL of 20% methylamine aqueous solution was added to the reaction solution, and the resultant was stirred with a vortex mixer to perform an amidation reaction (through this operation, the lactonized α2,3-sialic acids were to be methylamidated through aminolysis).

Purification with HILIC Column

To the reaction solution after the amidation reaction, 140 μL of ACN was added for dilution, and excessive reagents were removed by using a HILIC Tip (GL-Tip Amide, a custom-made product from GL Sciences, Inc., packed with a carrier for an Inertsil Amide analytical column (hereinafter, simply referred to as "Inertsil Amide") from the same company) as a pretreatment column for centrifugation. The Inertsil Amide is a carrier obtained by chemically-modifying silica gel with an amide group (carbamoyl group), and the recommended pH in using for HPLC is 2 to 7.5. The reaction solution diluted with ACN was added to a GL-Tip Amide, and passed therethrough by centrifugation at 4000×g to allow the glycan to be adsorbed on the carrier. Thereafter, 100 μL of 90% ACN/0.1% TFA solution was passed twice therethrough for washing, and 20 μL of $H_2O$ was passed twice therethrough and 20 μL of 90% ACN/0.1% TFA solution was passed once therethrough for elution of the glycan, and the eluate was subjected to evaporation to dryness by using a SpeedVac (Thermo Fisher Scientific). Thereafter, the sample subjected to evaporation to dryness was redissolved to prepare a solution, which was passed through a Stage Tip Carbon to be desalted. The Stage Tip Carbon is a carbon column prepared by cutting an Empore Disk-Carbon (produced by 3M Company) into pieces having a diameter of approximately 1 mm and packing a 200 μL tip with the pieces.

Mass Spectrometry

Figure 2B:
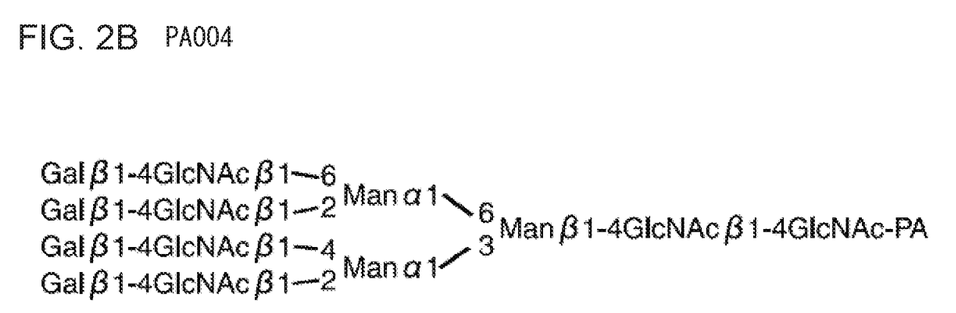
FIG. 2B shows a diagram illustrating a structure of a glycan used in an Example and Comparative Examples.

To the eluate from the Stage Tip Carbon, 200 fmol of the tetraantennary neutral glycan PA004 (Takara Bio Inc., the structure is illustrated in FIG. 2B) as an internal standard was added, and subjected to evaporation to dryness together with the sample. Thereafter, the sample was redissolved in 5 μL of water, and 1 μL was taken therefrom and dropped on a μFocus MALDI plate 700 μm (Hudson Surface Technology, Inc.). To the dropped sample, 0.75 μL of 3AQ/CA (3-aminoquinoline/p-coumaric acid) matrix solution containing 2 mM ammonium dihydrogen phosphate was added, and the plate was heated to 75° C. to remove residual solvent. Thereafter, by using a time-of-flight mass spectrometer (AXIMA-Resonance, Shimadzu/Kratos), ionization was performed by MALDI and measurement was performed in the negative ion mode.

Figure 3:
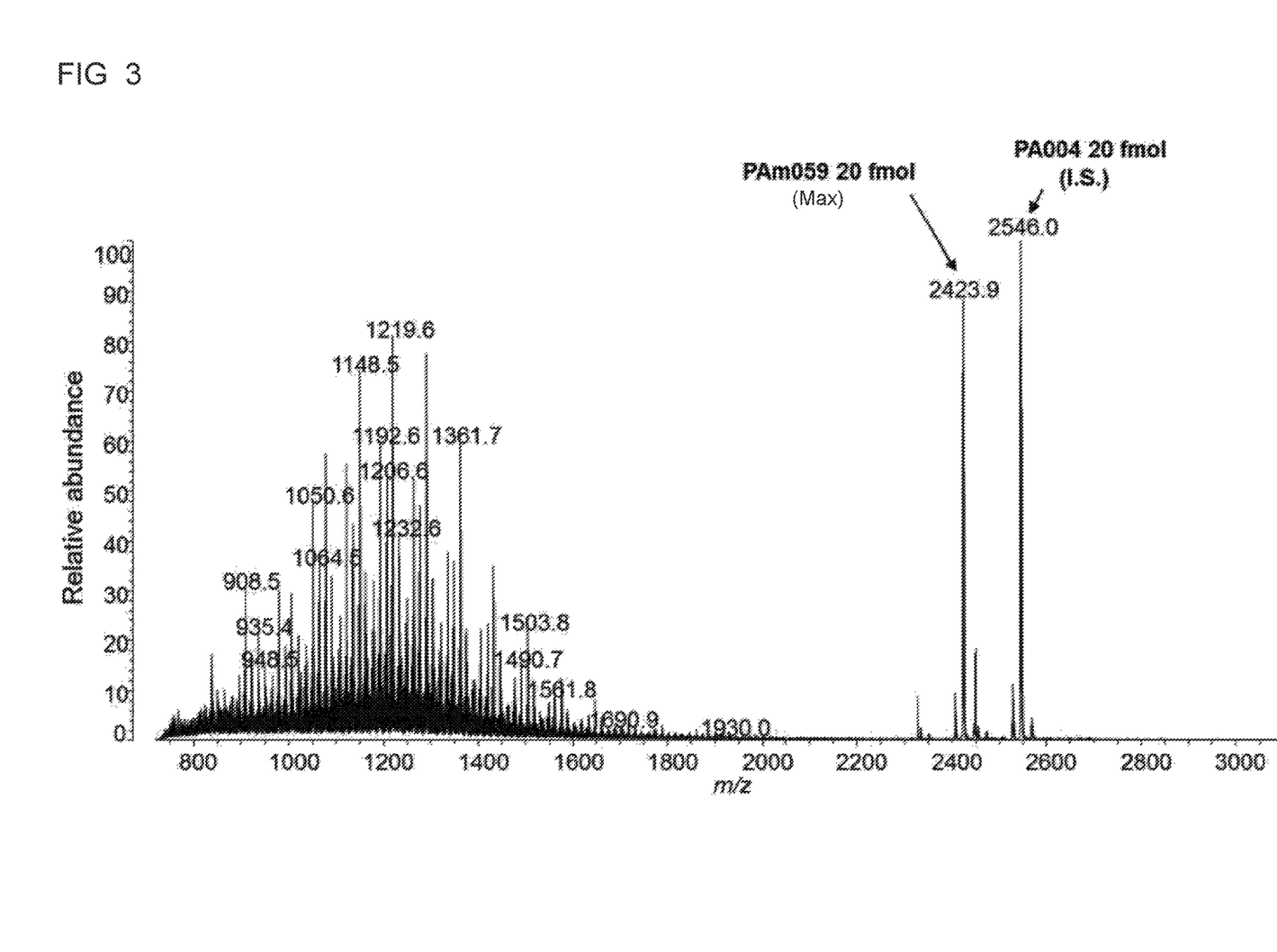
FIG. 3 shows a mass spectrum acquired in mass spectrometry in the negative ion mode for an analytical sample obtained by diluting a sample containing an acidic glycan subjected to an amidated reaction with acetonitrile (ACN), and then introducing the sample into a HILIC column.

FIG. 3 shows a mass spectrum acquired through mass spectrometry for Comparative Example 1. In the present conditions, the PA-labeled neutral glycan as the internal standard (I.S.) is ionized as a phosphate adduct with negative charge. The PAm059 contained in the sample has been amidated, and hence is likewise ionized as a phosphate adduct. The peak at m/z 2423.9 corresponds to the phosphate adduct of methylamidated PAm059, and it is understood that sialic acids were neutralized by methylamidation through the series of operations. Strong signals expected to be derived from contaminants were observed, however, in a low-m/z region such as a region of m/z 2000 or lower, and hence the preparation method of the Comparative Example was not available for practical use. In addition, s/n (signal-to-noise ratio) was low, which was inferred to be the impact of contaminants, similarly.

Example 1: Example Using Neutral Glycan

Figure 2C:
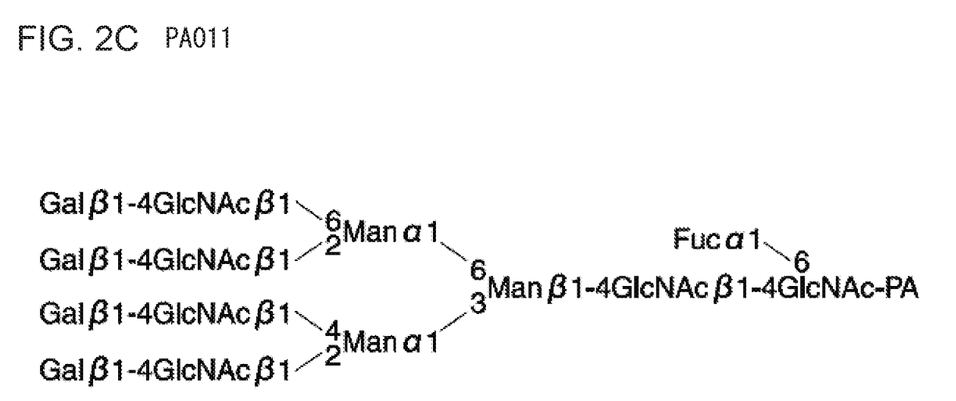
FIG. 2C shows a diagram illustrating a structure of a glycan used in an Example and a Comparative Example.

In the experiment system of Comparative Example 1, the sample recovery rate cannot be evaluated correctly. For this reason, evaluation was performed by using a PA-labeled neutral glycan, which does not change through lactone formation or aminolysis. To the eluate eluted from a HILIC column, PA011 (Takara Bio Inc., the structure is illustrated in FIG. 2C) as an internal standard (I.S.) was added, and the recovery rate was evaluated on the basis of relative intensity to that of the internal standard.

Lactonization Reaction and Amidation Reaction

A 100 fmol sample of the tetraantennary neutral glycan PA004 (Takara Bio Inc.) was subjected to evaporation to dryness in an Eppendorf tube. Subsequently, 20 μL of the above lactonization reaction solution was added thereto and reacted with stirring for 1 hour, and then 20 μL of 20% methylamine aqueous solution as an amidation reaction solution was added thereto, and the resultant was stirred with a vortex mixer to provide conditions to allow the occurrence of aminolysis.

Purification with HILIC Column

In dilution before purification with a HILIC Tip, the sample was divided into three portions, to which 140 μL of (a) ACN, 140 μL of (b) ACN containing 4% TFA, and 140 μL of (c) ACN containing 5% TFA were added, respectively. After dilution, pH was examined with a strip of pH test paper to find that pH was 12 or higher for (a), about 8 for (b), and about 3 for (c). The solutions were purified with a HILIC Tip, and then desalted with a Stage Tip Carbon, and subjected to evaporation to dryness by using a SpeedVac.

Mass Spectrometry

Thereafter, the sample was redissolved in 5 μL of water, and 1 μL was taken therefrom and dropped on a μFocus MALDI plate 700 μm (Hudson Surface Technology, Inc.). To the dropped sample, 0.75 μL of 3AQ/CA matrix solution containing 2 mM ammonium dihydrogen phosphate was added, and the plate was heated to 75° C. to remove residual solvent. Thereafter, by using a time-of-flight mass spectrometer (AXIMA-Resonance, Shimadzu/Kratos) ionization was performed by MALDI and measurement was performed in the negative ion mode.

Figure 4:
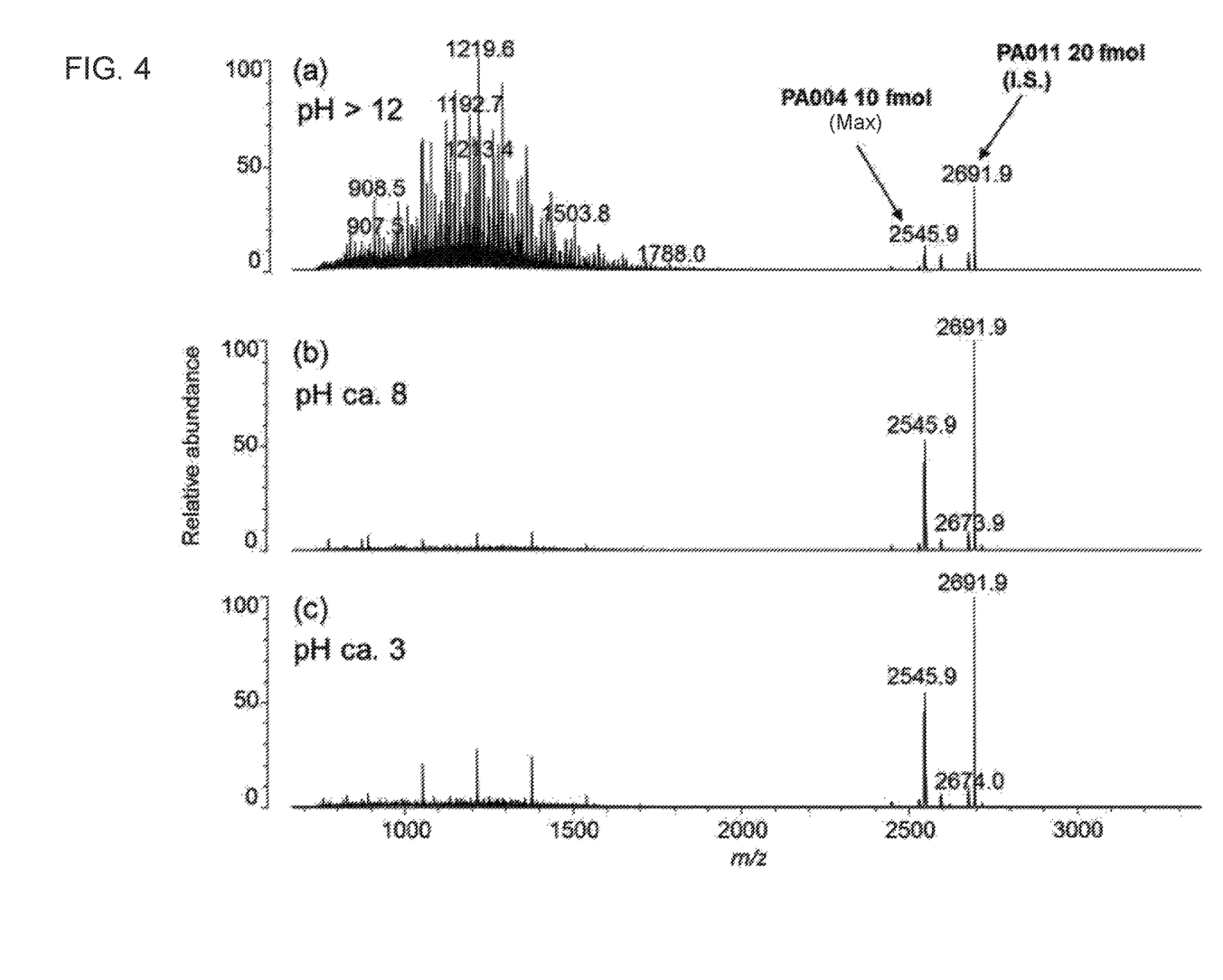
FIG. 4 shows mass spectra acquired in mass spectrometry in the negative ion mode for analytical samples obtained by diluting samples containing a neutral glycan subjected to an amidated reaction with ACN (top), 4% trifluoroacetic acid (TFA)/ACN solution (middle), and 5% TFA/ACN solution (bottom), respectively, and then introducing each sample into a HILIC column.

FIG. 4 shows a mass spectrum acquired through mass spectrometry for Example 1. In the present conditions, the PA-labeled neutral glycan is ionized as a phosphate adduct with negative charge. The relative intensity ratio between PA004 and PA011 after purification with a HILIC column was fitted to a calibration curve acquired in advance to evaluate the recovery rate. In measurement to acquire the calibration curve, dilution series of PA004 (25 fmol, 50 fmol, 100 fmol, 200 fmol) were added to a specific amount of PA011 (100 fmol), and the resultants were once subjected to evaporation to dryness, and negative ion mass spectra were acquired by a measurement method that is the same as the above procedure, without performing purification with a HILIC column. The calibration curve was acquired from the relative intensity ratios between PA004 and PA011.

For (a), which corresponds to the mass spectrum in the top of FIG. 4, strong signals inferred to be derived from contaminants were observed in a low-mass region such as a region of m/z 2000 or lower. For (b) and (c), which correspond to the mass spectra in the middle and bottom of FIG. 4, respectively (with pH control (quenching) using an acidic solution), a contaminant signal as observed for (a) was not observed. The sample recovery rate was about 40% for (a), and calculated to be 67% and 70% respectively for (b) and (c), from which it is understood that the recovery rate itself was also improved through quenching. These recovery rates are those after carbon purification performed in addition to HILIC purification after quenching, and can be said to be excellent, in view of the situation that a trace amount, 200 fmol, of glycans was handled. That is, it was found that quenching can reduce contamination from a HILIC carrier and in addition improve the recovery rate after purification.

Comparative Example 2: Comparison of Purification with Different Amide Carrier

As Comparative Example 2, it will be demonstrated that signals corresponding to contaminants are observed also when purification is performed by using an amide carrier different from the amide carrier used in Comparative Example 1 and Example 1. Comparison was made between a case where a tip including an Inertsil Amide carrier was used as a HILIC column (column A) and a case where a tip including an InertSustain Amide carrier (GL Sciences, Inc.) was used as a HILIC column (column B) in the method for (a) (conditions without quenching) in Example 1. The InertSustain Amide is a carrier obtained by chemically modifying silica gel with an amide group (carbamoyl group), and the recommended pH in using for HPLC is 2 to 8.5.

Figure 5:
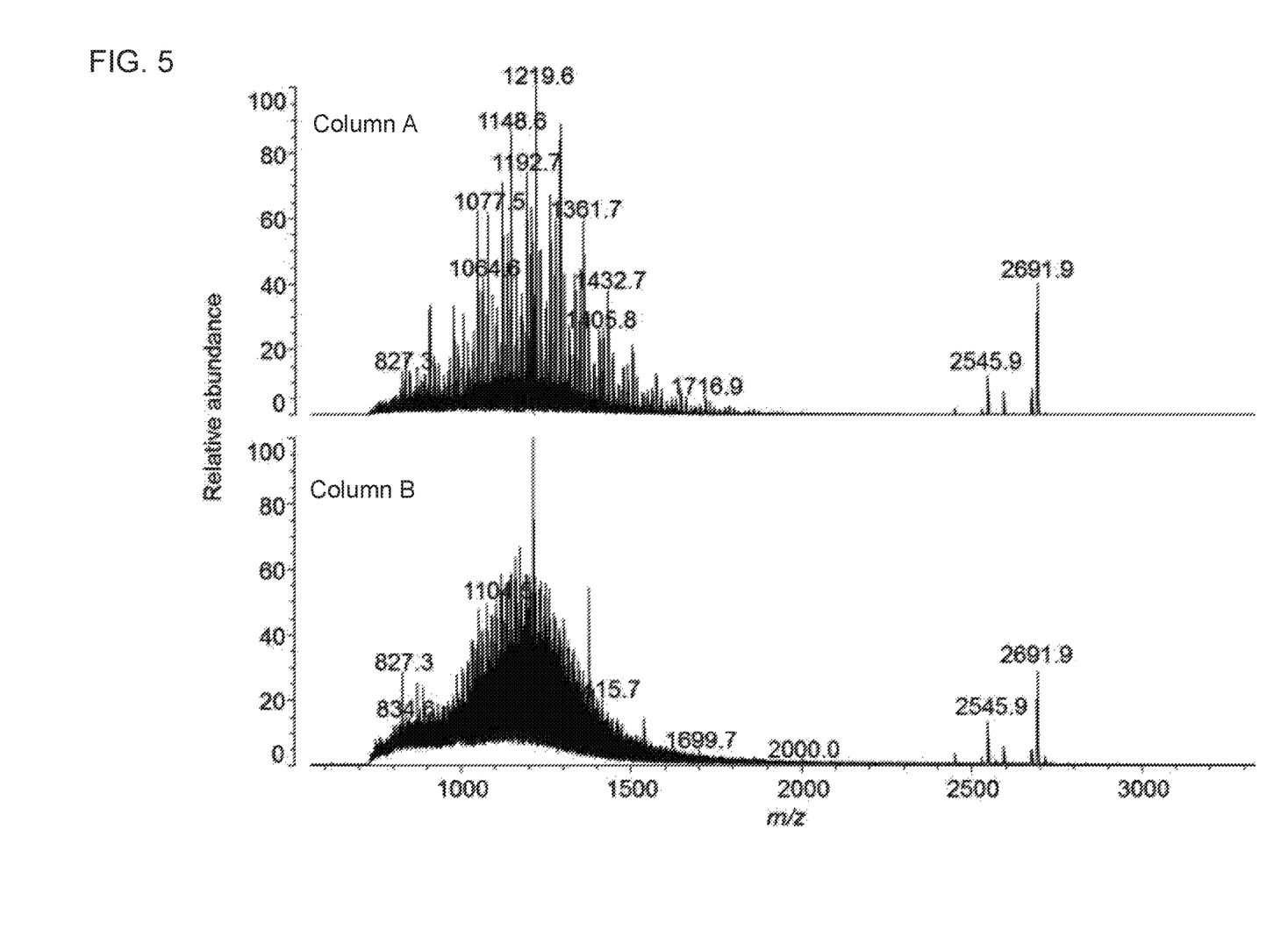
FIG. 5 shows mass spectra acquired in mass spectrometry in the negative ion mode for analytical samples obtained by diluting samples containing a neutral glycan subjected to an amidation reaction with ACN, and then introducing the samples respectively into a column A (recommended pH: 2 to 7.5) and a column B (recommended pH: 2 to 8.5) for HILIC.

FIG. 5 shows mass spectra obtained through mass spectrometry for Comparative Example 2. The recovery rate with the column A was approximately 40%, and 70% with the column B. Even with the column B, however, signals corresponding to contaminants were observed in a low-m/z region such as a region of m/z 2000 or lower, though the pattern was different, more strongly suggesting that introduction of solution at a pH deviating from the recommended pH damages the HILIC carrier.

The invention claimed is:

1. A method for preparing an analytical sample for analysis of a glycan contained in a sample, the method comprising:
    performing an amidation reaction that amidates a lactone structure included in the glycan through contacting the sample with a reaction solution that has a pH of higher than 10;
    adding an acidic solution to the reaction solution after the amidation reaction; and
    purifying the sample contained in the reaction solution by using a carrier for hydrophilic interaction chromatography after the acidic solution is added to the reaction solution, wherein:
    the amidation reaction amidates the lactone structure included in the glycan by aminolysis based on an interaction between an amino group and a lactone;
    the reaction solution comprising at least one selected from the group consisting of ammonia, a primary amine, and a salt thereof;
    wherein the concentration of ammonia, a primary amine, or a salt thereof in the reaction solution is 0.5 M or more;
    a time during which the sample is in contact with the reaction solution for the amidation reaction is shorter than 30 minutes;
    performing a lactonization reaction that lactonizes at least a part of sialic acids included in the glycans before the amidation reaction, wherein in the lactonization reaction, at least one selected from the group consisting of α2,3-sialic acid, α2,8-sialic acid, and α2,9-sialic acid among the sialic acids is lactonized;
    an operation that reacts the sample with a dehydration condensation agent is not performed after the addition of the reaction solution to the sample, wherein: the reaction solution does not include a dehydration condensation agent that is reacted with the lactones, and wherein only contacting the sample with the amidation reaction solution is performed for the amidation reaction;
    pH of the reaction solution after the acidic solution is added to the reaction solution is 10 or lower; and
    the amidation reaction is performed in a liquid phase.

2. The method for preparing an analytical sample according to claim 1, the method further comprising:
    performing a lactonization reaction that lactonizes at least a part of sialic acids included in the glycans before the amidation reaction.

3. The method for preparing an analytical sample according to claim 2, wherein
    the lactonization reaction is performed through contacting the sample with a lactonization reaction solution containing a dehydration condensation agent.

4. The method for preparing an analytical sample according to claim 3, wherein
    the reaction solution to be used for the amidation reaction contains ammonia or an amine,
    the lactonization reaction solution further contains a nucleophilic agent that is reacted with a sialic acid included in the glycan,
    the nucleophilic agent is different from ammonia or the amine contained in the reaction solution to be used for the amidation reaction, and
    in the lactonization reaction, a part of the sialic acids is lactonized based on a linkage type of the sialic acid, and at least a part of the nucleophilic agent is linked to another part of the sialic acids through addition of the lactonization reaction solution to the sample.

5. The method for preparing an analytical sample according to claim 2, wherein
    at least one selected from the group consisting of α2,3-sialic acid, α2,8-sialic acid, and α2,9-sialic acid among the sialic acids is lactonized in the lactonization reaction.

6. The method for preparing an analytical sample according to claim 3, wherein
    at least one selected from the group consisting of α2,3-sialic acid, α2,8-sialic acid, and α2,9-sialic acid among the sialic acids is lactonized in the lactonization reaction.

7. The method for preparing an analytical sample according to claim 4, wherein
    at least one selected from the group consisting of α2,3-sialic acid, α2,8-sialic acid, and α2,9-sialic acid among the sialic acids is lactonized in the lactonization reaction.

8. The method for preparing an analytical sample according to claim 4, wherein
    α2,3-sialic acid is lactonized and a part of the nucleophilic agent is linked to α2,6-sialic acid through addition of the lactonization reaction solution to the sample in the lactonization reaction.

9. The method for preparing an analytical sample according to claim 1, wherein
    the acidic solution is a solution containing 0.2% by weight or more of trifluoroacetic acid.

10. An analysis method comprising:
    preparing an analytical sample by using the method for preparing an analytical sample according to claim 1; and
    analyzing the prepared analytical sample.

11. The analysis method according to claim 10, wherein the prepared analytical sample is analyzed through at least one of mass spectrometry and chromatography.

12. The method for preparing an analytical sample according to claim 1, wherein
the reaction solution that has a pH of 12 or higher.

13. The method for preparing an analytical sample according to claim 1, wherein
the amidation reaction amidates the lactone structure included in the glycan by aminolysis and
the reaction solution comprising at least one selected from the group consisting of ammonia, an amine, and a salt thereof.

14. The method for preparing an analytical sample according to claim 1, wherein
the amine is a primary amine.

15. The method for preparing an analytical sample according to claim 1, further comprising:
performing a lactonization reaction that lactonizes at least one of α2,8-sialic acid and α2,9-sialic acid included in the glycans.

* * * * *